(12) United States Patent
Lang et al.

(10) Patent No.: US 8,173,941 B2
(45) Date of Patent: May 8, 2012

(54) APPARATUS FOR MICROWAVE-ASSISTED PREPARATION OF SPECIMENS

(75) Inventors: Anton Lang, Vienna (AT); Paul Wurzinger, Deutsch-Wagram (AT); Rainer Wogritsch, Vienna (AT); Christian Peinhopf, Graz-Webling (AT); Peter Kettisch, Graz-Webling (AT)

(73) Assignee: Leica Mikrosysteme GmbH, Vienna (AT)

( * ) Notice: Subject to any disclaimer, the term of this patent is extended or adjusted under 35 U.S.C. 154(b) by 1260 days.

(21) Appl. No.: 11/860,824

(22) Filed: Sep. 25, 2007

(65) Prior Publication Data

US 2008/0078757 A1    Apr. 3, 2008

(30) Foreign Application Priority Data

Oct. 3, 2006 (AT) ................ A 1648/2006

(51) Int. Cl.
 *H05B 6/64* (2006.01)
(52) U.S. Cl. ............... 219/679; 219/686; 73/863.11
(58) Field of Classification Search ............ 219/679, 219/718, 696, 711, 744, 746, 686, 693, 756; 422/186, 64, 549, 78, 90, 28, 29, 40; 435/40.5, 435/7.21, 40.51, 1.3; 73/863.11, 863.23, 73/863.12
See application file for complete search history.

(56) References Cited

U.S. PATENT DOCUMENTS

| | | | |
|---|---|---|---|
| 4,681,740 A | 7/1987 | Commarmot et al. | |
| 4,693,867 A | 9/1987 | Commarmot et al. | |
| 5,382,414 A | 1/1995 | Lautenschlager | |
| 5,447,077 A * | 9/1995 | Lautenschlager | 73/863.11 |
| 5,459,302 A | 10/1995 | Jacqualt | |
| 5,620,659 A | 4/1997 | Revesz | |
| 6,744,024 B1 | 6/2004 | Hayes et al. | |
| 6,753,517 B2 | 6/2004 | Jennings | |
| 6,875,583 B2 | 4/2005 | Giberson et al. | |
| 6,917,023 B2 | 7/2005 | Hayes et al. | |
| 2002/0090736 A1 | 7/2002 | Ulin | |

FOREIGN PATENT DOCUMENTS

| | | |
|---|---|---|
| EP | 0350271 B1 | 6/1994 |
| EP | 1605243 A1 | 12/2005 |
| WO | 8805906 A1 | 8/1988 |
| WO | 99/09390 | 2/1999 |
| WO | 01/44783 A1 | 6/2001 |
| WO | 01/44784 A1 | 6/2001 |
| WO | 2005/040763 A1 | 5/2005 |

* cited by examiner

*Primary Examiner* — Quang Van

(74) *Attorney, Agent, or Firm* — Hodgson Russ LLP

(57) ABSTRACT

In an apparatus for microwave-assisted preparation of specimens with a microwave generator (1), a microwave chamber for receiving specimens (5) to be processed, and a container arrangement (11) for a number of containers (9) for liquids, the microwave chamber is realized as a waveguide (2) that includes a first opening (7a) for introduction of a specimen (5) and a second opening (8a), preferably arranged at the bottom, through which a liquid container (9) is reversibly introduced into the microwave chamber while the specimen (5) is held stationary, until the liquid container thus introduced into the microwave chamber, and the liquid contained therein, surround the specimen (5).

17 Claims, 4 Drawing Sheets

APPARATUS FOR MICROWAVE-ASSISTED PREPARATION OF SPECIMENS

CROSS REFERENCE TO RELATED APPLICATIONS

This application claims priority of Austrian patent application A 1648/2006 filed Oct. 3, 2006, which is incorporated by reference herein.

FIELD OF THE INVENTION

The present invention relates to an apparatus for microwave-assisted preparation of specimens, having at least one microwave generator, a microwave chamber for receiving at least one specimen to be processed, and having a container arrangement for at least two containers for liquids to surround, inside the microwave chamber, the specimen(s) that are to be processed.

BACKGROUND OF THE INVENTION

The preparation of biological specimens is performed, for example, for the purpose of electron-microscope examination. Microwaves are used in this context to excite and accelerate the fixation, substitution, infiltration, and polymerization processes. The overall time for preparation processes can thereby be greatly reduced.

A microwave-assisted device for extracting substances from a starting material is described in U.S. Pat. No. 5,620,659. A number of specimen holders are mounted in a carousel-like turntable and placed, as a whole, in a multimode chamber. Conduits from each specimen holder lead into a collection container that can additionally be pumped down in order to avoid contamination of the multimode chamber with escaped gases.

U.S. Pat. No. 6,875,583 discloses a device for rapid microwave-assisted fixation of tissue. Biological prepared samples are positioned, in a formalin solution serving as a fixing agent, in the microwave field of a multimode chamber. The microwave power output is controllable. The temperature is controlled by pump-circulating and cooling the fixing solution outside the microwave field.

The pump-circulating and cooling of reagents during the processing of biological samples has the disadvantage that reagent replacement entails considerable complexity. Valves, pumps, and reservoir and waste containers must be provided. In U.S. Pat. No. 6,875,583 the use of the disclosed invention is therefore limited to one specific process step. A relatively high consumption of chemicals is also associated with an arrangement of this kind, since not only the process vessel but additionally the entire cooling circuit must be filled. The replacement and replenishment of reagents must also encompass washing steps for the cooling circuit.

Multimode microwave chambers, i.e. chambers such as a household microwave oven having relative large chamber dimensions, exhibit large local inhomogeneities in microwave intensity (so-called "hot spots" and "cold spots"). Apparatuses for homogenizing the microwave field are therefore necessary in order to create defined and reproducible process conditions.

U.S. Pat. No. 4,681,740 and U.S. Pat. No. 5,459,302 disclose the arrangement of reaction vessels in a microwave field that is constituted in a waveguide. The receptacle for a reaction vessel is embodied so that the lower end of the vessel is located in the wave field, and the upper end projects out of the waveguide. The projecting part is surrounded by a tube that prevents the emergence of microwaves. The temperature of the reaction vessel can be monitored by way of a pyrometer.

U.S. Pat. Nos. 6,753,517, 6,917,023, and 6,744,024 disclose devices for microwave-assisted chemical synthesis. The reagents are located in a microwave-transparent reaction vessel that is positioned inside the internal cavity of a microwave resonator shaped like a cylindrical ring; the specimen is not, however, located in the actual waveguide that annularly surrounds the cavity. Apertures in the inner waveguide wall cause microwave radiation to travel to the reaction vessel. A comparatively homogeneous distribution of the microwave radiation field over the region in which the reaction proceeds is thereby achieved, but this arrangement requires additional complex sealing of the microwave radiation toward the outside. The temperature in the reaction vessel is monitored by a sensor, and is controlled by regulating the microwave power output or by cooling the outer shell of the reaction container with the aid of a flow of gas or liquid.

The above-described methods for microwave-assisted preparation require a manual replacement of the reagents when the specimens are to be processed sequentially in different liquids, and are therefore labor-intensive. In conventional tissue processors, specimen processing takes from several hours (e.g. 24 hours) to days, depending on the protocol. Only after this long waiting time are the specimens therefore available for examinations in the electron microscope.

It is additionally known, in the context of the processing of specimens in a sequence of liquids, to place said liquids in a turntable carrier (a so-called carousel), and for the specimen to be immersed sequentially, in a process device, into the liquids present in the carousel. A usual procedure for this is to rotate the carousel beneath the specimen so that the liquid to be utilized becomes positioned below the specimen, and then the entire carousel is raised until the specimen is immersed. The desired process step can then take place, additionally (if necessary) with the use of a heating system or like. The carousel is then lowered, rotated further, and so on. This procedure is of little advantage in connection with microwave radiation, since a carousel is too bulky for introduction into a waveguide, or the entire carousel would need to be placed into a waveguide (as in U.S. Pat. No. 5,620,659), although the liquids not being used would also be affected by the microwave radiation.

SUMMARY OF THE INVENTION

It is an object of the present invention to make available a device with which the specimens can be processed, rapidly and with reduced handling complexity, in a succession of processing fluids inside a microwave chamber.

This object is achieved by a device of the kind cited initially in which the microwave chamber is realized as a waveguide that comprises
 at least one opening of a first kind for introduction of the at least one specimen, and
 at least one opening of a second kind through which at least one liquid container is reversibly introducible into the microwave chamber while the specimen is held stationary,
such that a liquid container introduced into the microwave chamber surrounds at least one specimen.

This approach allows the processing of specimens in multiple liquids to be combined with the possibility of switching in a homogeneous and reproducible microwave field, thereby enabling fast, preferably automated, specimen processing with few user interventions.

In contrast to known microwave devices that possess only one opening through which liquids can be introduced into the reaction chamber, the invention provides for separate introduction of the specimen and the processing liquid into the microwave chamber. Specimens can thus be placed in stationary fashion in the chamber, and processed in the succession of liquids.

In a preferred embodiment, the waveguide is embodied as a monomode waveguide, which additionally improves homogeneity and reproducibility.

Advantageously, at least one closure means is provided with which the at least one opening of a first kind is sealable in microwave-tight fashion during operation of the apparatus. Not only does this prevent contamination of the surrounding area with microwave radiation, but the homogeneity and stability of the microwave field in the wave guide is also greatly improved. The closure means can be joined to a retaining apparatus for the specimen(s), thereby resulting in unambiguous positioning of the specimens within the waveguide and at the same time preventing the waveguide from inadvertently remaining unclosed.

An attenuator tube that prevents the emergence of microwave radiation can favorably be provided on the opening of a second kind, so that the interior of the microwave chamber is accessible without a cover or the like, and the transport of liquid containers into and out of the chamber is greatly simplified.

For positioning of the containers, a container arrangement having a number of receiving openings, each for removable retention of one liquid container, is particularly useful, the position of the container arrangement being adjustable (e.g. in steps) between positions in each of which a different liquid container is located in a removal position next to an opening of a second kind; also a delivery apparatus which is set up to remove a liquid container from the removal position, introduce it into the waveguide, and put it back into the removal position at a later point in time. The container arrangement can be realized using a turntable apparatus rotatable about a shaft, on which apparatus receiving openings are positionable along a ring. It is furthermore advantageous if, for example when working with volatile and/or toxic liquids, a respective cover is provided on the container arrangement for at least some of the receiving openings, with which covers liquid containers retained in the receiving openings are closable independently of one another. An opening apparatus can be provided for opening the cover of the liquid container that is in the removal position.

In a simple geometry, the openings of a first kind and of a second kind are located respectively opposite one another, the opening of a second kind being arranged on the underside of the waveguide.

In order to enhance safety, in particular when flammable liquids are being used, an extraction tube attached to the microwave chamber, through which tube gases in the microwave chamber are extractable, is favorable. The gas composition in the microwave chamber can be monitored by means of an additional gas sensor provided on the microwave chamber or the extraction tube; by means thereof, microwave inputs can be shut off upon exceedance of a limit value, for example the concentration of a specific gas component. A temperature sensor, in particular an IR sensor, provided on the microwave chamber can furthermore be present in order to monitor the temperature of the specimen(s) present in the microwave chamber.

Extensive automation of the apparatus is favorable in order to increase process reliability, in particular when all motion axes are motorized and the motions are centrally controllable by a control unit. This can be effected by a control unit for central control of the motor-assisted motions, in particular of the introduction and outward movement of the liquid containers into and from the waveguide. The control unit can also be set up to control the intensity of the microwave emission and thereby to regulate the process temperature for each liquid container that is introduced into the waveguide. In addition, good mixing of the liquids and rapid exchange of liquid boundary layers on the specimen(s) can be achieved by way of a continuous up-and-down motion of small amplitude (i.e. within the homogeneity range of the microwave field in the waveguide) during microwave application. For this purpose, the control unit can be set up to control a repeated up-and-down motion of the at least one specimen of this kind during microwave application.

BRIEF DESCRIPTION OF THE DRAWING FIGURES

Further examples of possible configurations of the disclosed device, as well as preferred embodiments, are described below with reference to the appended Figures, in which:

FIG. 1 schematically depicts a first embodiment of the invention, in a sectioned view in which vessels having various liquids are lifted out of a rotatable carousel into the wave guide;

DETAILED DESCRIPTION OF THE INVENTION

The embodiments shown here are to be understood as examples, and do not represent any limitation of the invention to the embodiments that are presented.

Figure 1:
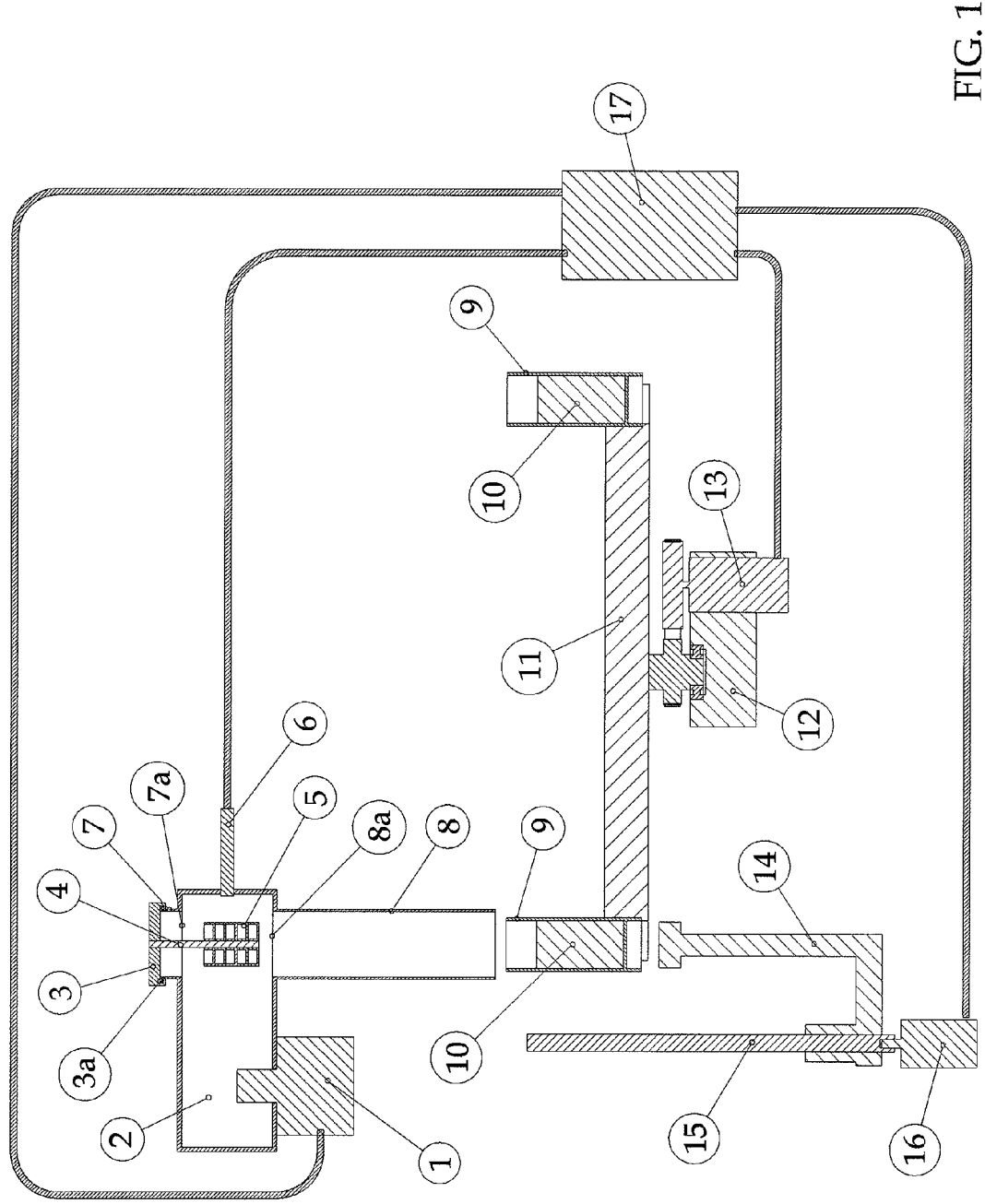

FIG. 1 shows a first preferred exemplifying embodiment of the invention: an apparatus for microwave-assisted preparation of specimens, in particular biological specimens. A wave guide 2 is embodied as a monomode guide, for example in the form of a rectangular guide. Microwaves of a specific mode generated by a magnetron 1 propagate therein, such that essentially a standing wave having a constant time-averaged energy distribution is formed in wave guide 2. In the region of a maximum of the energy distribution, the wave guide possesses two vertically oppositely located openings 7a, 8a. Set onto these openings are tubes 7, 8 that prevent the emergence of microwaves. Upper tube 7 is closed off for this purpose with a cover 3 that is embodied in such a way that microwaves cannot emerge either through it itself or through gap 3a with respect to tube 7. Lower tube 8 is embodied as an attenuation tube that produces a substantial attenuation (e.g. 60 dB) over its length, so that microwaves cannot emerge to an appreciable extent through the outer opening (facing downward in the Figure) of tube 8. This tube can therefore remain open even during microwave operation and thus enables, in simple fashion, the introduction of vessels for an automated process.

Inserted into cover 3 is a retaining element 4 with which basket 5, having biological specimens, is retained in the region of the wave guide, both the retaining element itself and the specimen baskets being made of microwave-transparent material. Arranged beneath tube 8 is a carousel 11 whose rotation allows multiple containers 9, having liquids 10, to be positioned below tube 8. The liquid present in each liquid container can be, for example, a different reagent in each case for processing the specimens. The carousel shaft is mounted stationary in the device, but if necessary can be removed as a whole from bearing 12; in the position mounted on bearing 12, carousel 11 can be moved (rotated) by a motor 13. A lifting arm 14 made of microwave-transparent material can be moved upward via a spindle 15 driven with the aid of a motor 16, and in this fashion can introduce into the wave guide the particular vessel positioned below tube 8. In addition to plastics, machinable ceramics (e.g. MARCOR®) can be used as materials for lifting arm 14. In the topmost position of the lifting arm, baskets 5 having the specimens are completely immersed into liquid 10.

Vessels 9 present on carousel 11 can contain different reagents 10 and can be raised successively, or in any sequence, into the microwave chamber so that the vessel (and therefore the liquid contained therein) introduced into the microwave chamber surrounds basket 5. The motions are controlled by a control unit 17. Control unit 17 furthermore monitors microwave emission and measures the temperature of the liquids via an IR sensor 6. A controlled heating of the specimens and reagents in the chamber is therefore regulated. Control unit 17 can be programmed by the user so that each working step has one of reagents 10, and/or a specific application time and application temperature, associated with it. These programs are automatically executed by control unit 17. Because of the particular geometric arrangement, control unit 17 can move vessels 9 via lifting arm 14 even during microwave application. This is advantageously exploited in order to achieve, with the aid of a short-stroke up-and-down motion, a continuous exchange of the liquid boundary layers that are in direct contact with the specimens. Improved homogeneity and shorter durations for the preparation processes can thereby be achieved.

As already mentioned, the control unit controls the power output of the microwave during each individual working step; the output can also be regulated by the control unit so that a predetermined temperature is reached in liquid vessel 9. If necessary for selected (or all) steps, it is also possible to institute pulsed (i.e. intermittent) operation of the microwave instead of a respectively constant or (for example in the case of regulation to a specific temperature value) steady power output. As a rule, microwave power output is switched off between the individual steps.

Figure 2:
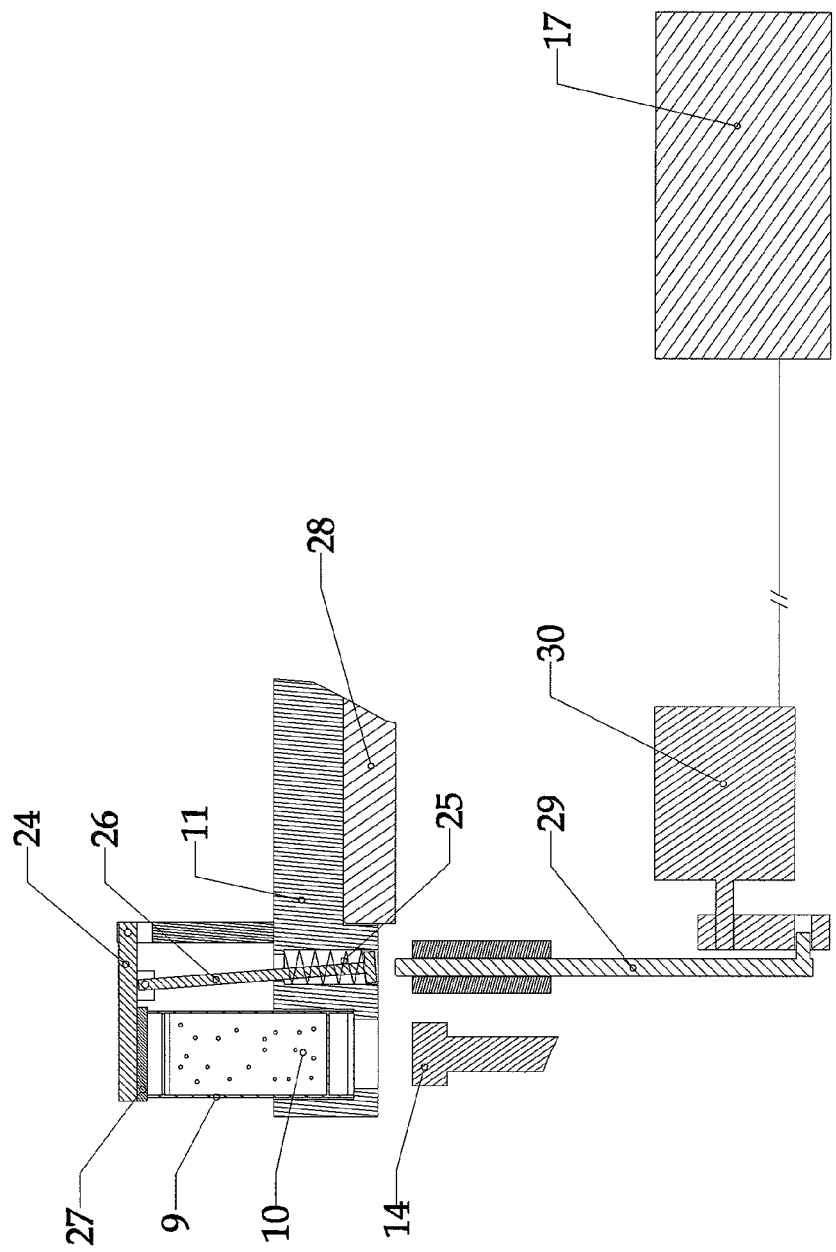
FIG. 2 shows a variant of the carousel with individually opened vessels.

Referring to FIG. 2, an advantageous embodiment of carousel 11 is configured so that vessels 9 present in the carousel can be closed off by container covers 24. Each container cover 24 is held shut by a spring 25 via a tension rod 26. In addition, an elastic support 27 can be mounted on the cover in order to ensure good closure on the part of the cover. The evaporation rate of liquids 10 is thereby minimized, and not only is the fill level held constant over a long period, but pollution of the surrounding atmosphere with toxic, flammable, or corrosive vapors is also greatly reduced. In this embodiment the carousel is advantageously separated into a carousel carrier 28 that is rotatably joined to bearing 12 and is not removable, and the actual carousel 11 carrying the covers. Carousel 11 having the closed vessels 9 can be separated from the carousel carrier 28 by the user, and safely transported to an enclosure where vessels 9 are filled and emptied.

It is immediately understandable that in the embodiment shown, container covers present on carousel 11 must be opened before a vessel 9 can be moved by lifting arm 14 in order to receive specimen basket 5. This is usefully effected by way of a plunger 29 that is actuated by a motor 30, for example via an eccentric; other types of actuation, such as e.g. via a spindle or any other suitable mechanical coupling, are of course also possible. The motions of motor 30 are once again controlled by control unit 17 so that in a coordinated motion sequence, vessel 9 is positioned by means of carousel 11, then container cover 24 is opened, and vessel 9 is then transported into the chamber with the aid of lifting arm 14.

Figure 3:
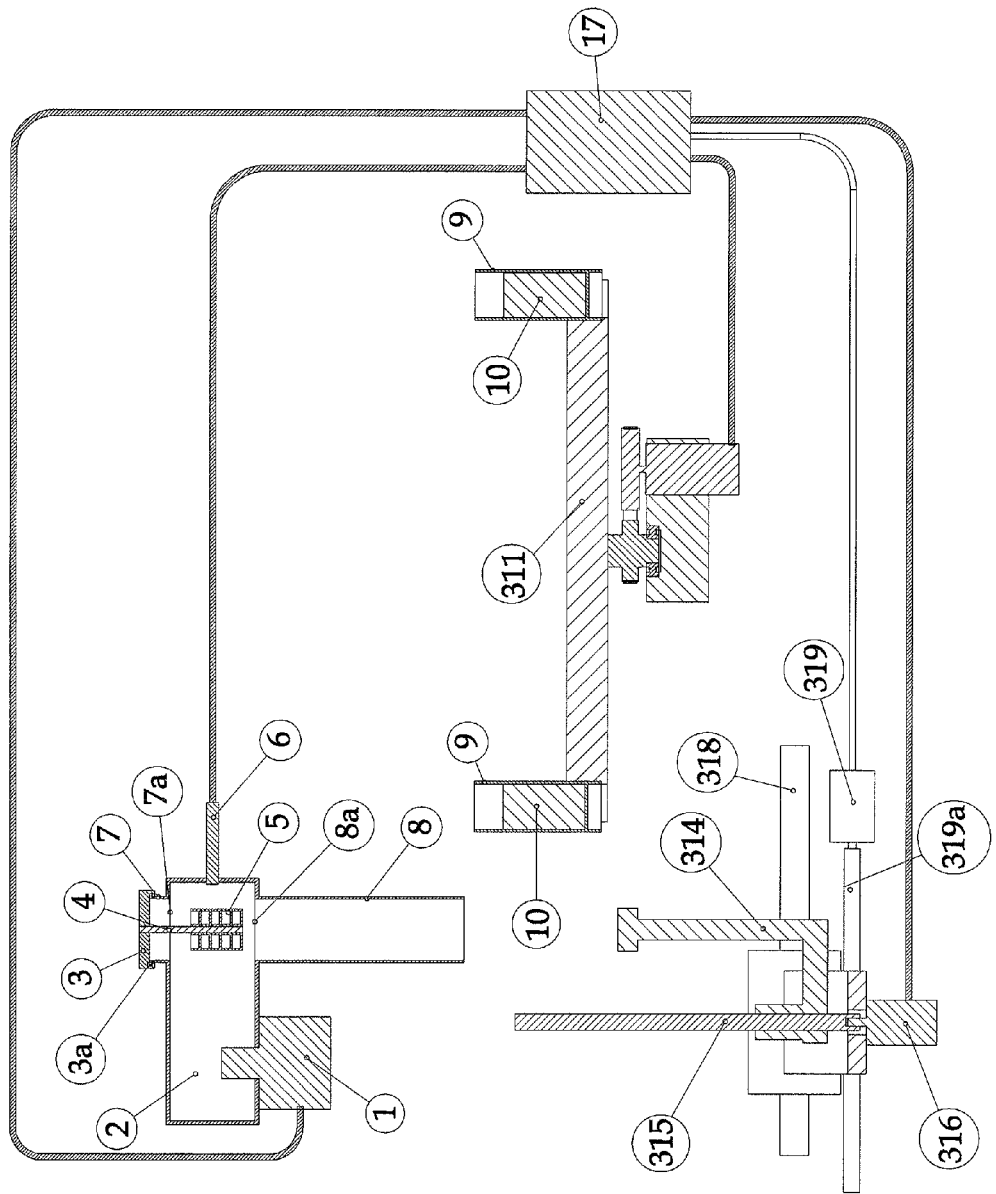
FIG. 3 shows a second embodiment of the invention with horizontal and vertical motion of the vessels.

FIG. 3 schematically depicts a second embodiment of the invention in which carousel 311 is not positioned directly below tube 8. Instead, vessels 9 removed from carousel 311 with lifting arm 314 are transferred via a further transport mechanism 318, for example with a spindle 319a, to a location beneath tube 8. Transport mechanism 318 is operated by a motor 319 that is controlled by control unit 17. Vertical lifting of the lifting arm is accomplished, in the manner corresponding to FIG. 1, via a spindle 315 driven with the aid of a motor 316.

Figure 4:
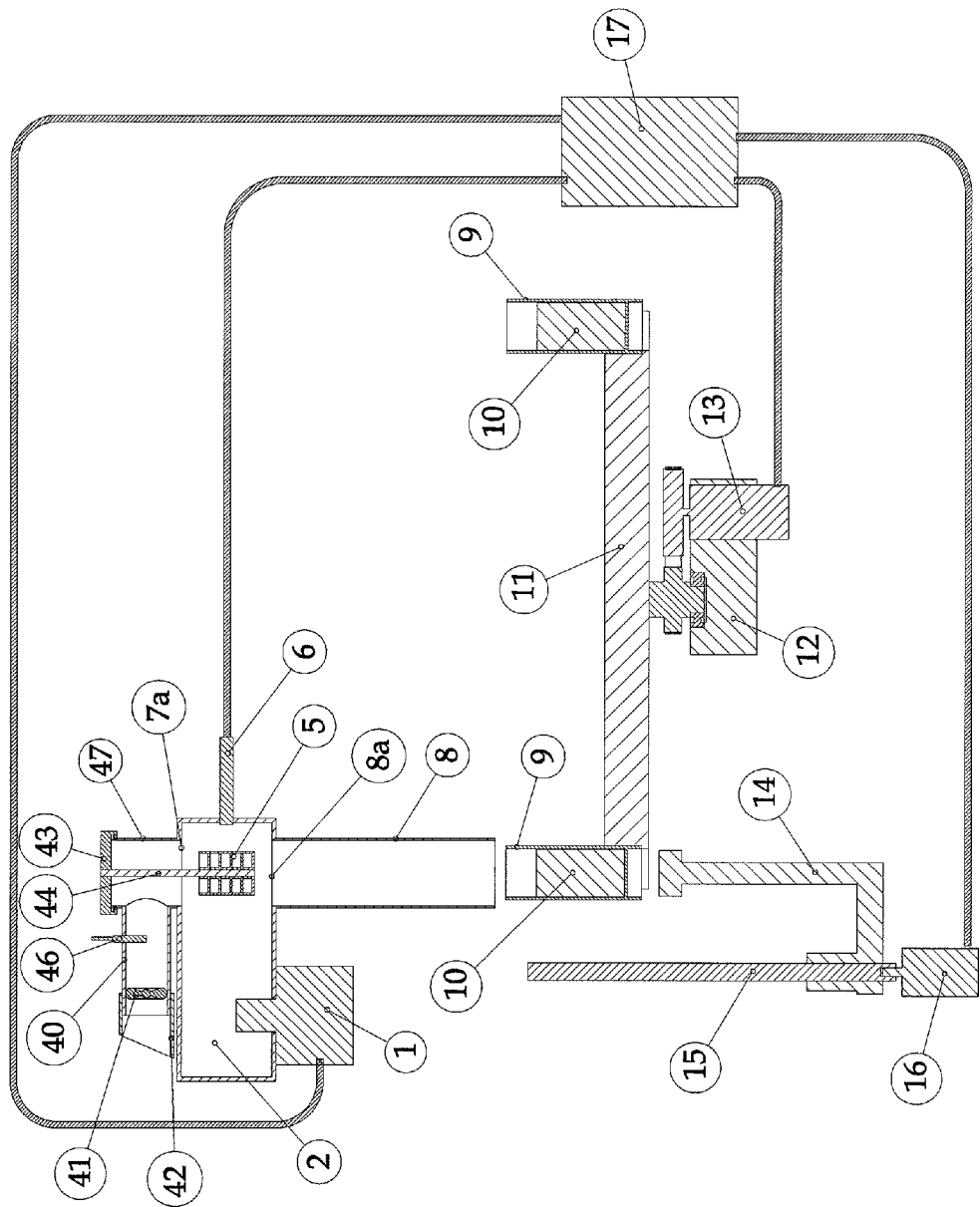
FIG. 4 shows a third embodiment of the invention with a gas extraction system on the wave guide.

FIG. 4 schematically depicts a third embodiment of the invention that is derived from the first embodiment but can also be combined with the second embodiment. Instead of upper tube 7 of the first embodiment, upper opening 7a is closed off by a tube 47 having an opening on which a further tube 40 is in turn mounted. Vapors occurring in the microwave chamber can be extracted through tube 40 with the aid of a fan 41, and delivered via a hose 42 to an exhaust system. The combination of tubes 47, 40 with cover 43 is once again embodied so that the emergence of microwaves is prevented by exponential attenuation; if applicable, a geometrically adapted retaining means 44 must be used. In this embodiment, a gas sensor 46 can additionally be used, which monitors the atmosphere in the chamber and results in a shutoff of microwave emission upon exceedance of a limit value.

What is claimed is:

1. An apparatus for microwave-assisted preparation of at least one specimen, the apparatus comprising:
    a container arrangement including a plurality of liquid containers for holding liquids intended to surround the at least one specimen;
    a microwave generator;
    a microwave chamber in communication with the microwave generator, the microwave chamber being a waveguide that includes an opening of a first kind through which the at least one specimen is introduced into the microwave chamber, and a bottom opening of a second kind through which a liquid container chosen from the plurality of liquid containers is substantially vertically introduced into the microwave chamber such that liquid contained therein surrounds the at least one specimen within the microwave chamber; and
    a lifting device for substantially vertically introducing the chosen liquid container into the microwave chamber.

2. The apparatus according to claim 1, wherein the waveguide is a monomode waveguide.

3. The apparatus according to claim 1, further comprising a cover associated with the opening of a first kind for preventing microwaves from escaping the microwave chamber through the opening of a first kind.

4. The apparatus according to claim 3, further comprising a retaining element connected to the cover for holding the at least one specimen stationary within the microwave chamber.

5. The apparatus according to claim 1, further comprising an attenuator tube associated with the opening of a second kind for preventing microwaves from escaping the microwave chamber through the opening of a second kind.

6. The apparatus according to claim 1, further comprising an extraction tube attached to the microwave chamber through which gases in the microwave chamber are extractable.

7. The apparatus according to claim 6, further comprising a gas sensor provided on the microwave chamber or the extraction tube for monitoring gas composition in the microwave chamber.

8. The apparatus according to claim 1, further comprising a temperature sensor provided on the microwave chamber for monitoring temperature of the at least one specimen present in the microwave chamber.

9. The apparatus according to claim 8, wherein the temperature sensor is an infrared temperature sensor.

10. An apparatus for microwave-assisted preparation of at least one specimen, the apparatus comprising:
a container arrangement including a plurality of liquid containers for holding liquids intended to surround the at least one specimen;
a microwave generator; and
a microwave chamber in communication with the microwave generator, the microwave chamber being a waveguide that includes an opening of a first kind through which the at least one specimen is introduced into the microwave chamber, and an opening of a second kind through which a liquid container chosen from the plurality of liquid containers is reversibly introduced into the microwave chamber such that liquid contained therein surrounds the at least one specimen within the microwave chamber;
wherein the container arrangement includes a plurality of receiving openings each for removable retention of one of the plurality of liquid containers, and the container arrangement is movable relative to the microwave chamber to position a selected one of the plurality of liquid containers in a removal position near the opening of a second kind, and the apparatus further comprises a lifting arm operable to remove a selected liquid container from the removal position, introduce the selected liquid container into the waveguide, and subsequently return the selected liquid container to the removal position.

11. The apparatus according to claim 10, wherein the container arrangement includes a turntable rotatable about a shaft, and the plurality of receiving openings are arranged on the turntable in a ring about the shaft.

12. The apparatus according to claim 10, wherein the container arrangement includes a container cover associated with a respective one of the plurality of receiving openings for closing a liquid container retained in the associated receiving opening.

13. The apparatus according to claim 12, further comprising an opening apparatus operable for opening the container cover on a liquid container in the removal position.

14. The apparatus according to claim 10, wherein the container arrangement is driven by a first motor and the lifting arm is driven by a second motor, and the apparatus further comprises a control unit connected to first and second motors for controlling motor-assisted motions of introduction and outward movement of the liquid containers into and from the waveguide.

15. The apparatus according to claim 14, wherein the control unit is further connected to the microwave generator for controlling intensity of microwave emission to regulate process temperature of a liquid container introduced into the waveguide.

16. The apparatus according to claim 14, wherein the control unit is operable to control the second motor to provide a repeated low-amplitude up-and-down motion of a liquid container relative to the at least one specimen during microwave application.

17. An apparatus for microwave-assisted preparation of at least one specimen, the apparatus comprising:
a container arrangement including a plurality of liquid containers for holding liquids intended to surround the at least one specimen;
a microwave generator; and
a microwave chamber in communication with the microwave generator, the microwave chamber being a waveguide that includes an opening of a first kind through which the at least one specimen is introduced into the microwave chamber, and an opening of a second kind through which a liquid container chosen from the plurality of liquid containers is reversibly introduced into the microwave chamber such that liquid contained therein surrounds the at least one specimen within the microwave chamber; and
wherein the openings of the first kind and of the second kind are located opposite one another, and the opening of the second kind is arranged on an underside of the waveguide.

* * * * *